(12) United States Patent
Zhang et al.

(10) Patent No.: US 11,420,925 B2
(45) Date of Patent: Aug. 23, 2022

(54) REDUCTION METHOD AND REDUCTION PRODUCT OF ALKENYL ACTIVE METHYLENE COMPOUND

(71) Applicant: SOOCHOW UNIVERSITY, Suzhou (CN)

(72) Inventors: Shilei Zhang, Suzhou (CN); Yujian Mao, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 17/200,647

(22) Filed: Mar. 12, 2021

(65) Prior Publication Data
US 2021/0198176 A1   Jul. 1, 2021

Related U.S. Application Data

(63) Continuation of application No. PCT/CN2018/105597, filed on Sep. 13, 2018.

(51) Int. Cl.
*C07C 67/303* (2006.01)
*B01J 27/13* (2006.01)
*C07C 231/12* (2006.01)

(52) U.S. Cl.
CPC ............. *C07C 67/303* (2013.01); *B01J 27/13* (2013.01); *C07C 231/12* (2013.01)

(58) Field of Classification Search
CPC ... C07C 231/12; C07C 67/303; C07C 235/80; C07C 69/616; B01J 27/13; B01J 2231/645; B01J 2531/824; B01J 31/0247; B01J 31/121; B01J 31/2239; B01J 31/30
See application file for complete search history.

(56) References Cited

FOREIGN PATENT DOCUMENTS

| CN | 107805200 | A |   | 3/2018 |
| CN | 108218672 |   | * | 6/2018 |
| CN | 109096105 |   | * | 12/2018 |
| CN | 109096105 | A |   | 12/2018 |
| WO | WO-2020051855 | A1 | * | 3/2020 |

OTHER PUBLICATIONS

WO2020/051855 translated (Year: 2020).*
CN109096105 translated (Year: 2018).*
Liu et al. (The Employment of Sodium Hydride as a Michael Donor in Palladium-catalyzed Reductions of alpha, beta-Unsaturated Carbonyl Compounds, Published Feb. 2019 (Year: 2019).*
Ye Liu et al., The Employment of Sodium Hydride as a Michael Donor in Palladium-catalyzed Reductions of a, b-Unsaturated Carbonyl Compounds, Adv. Synth. Catal. 20129, 361, 1554-1558 (Feb. 6, 2019).
Suckchang Hong et al., Efficient synthesis and biological activity of Psammaplin A and its analogues as antitumor agents, European Journal of Medicinal Chemistry 96 (2015) 218-230 (Apr. 6, 2015).
Egle M. Beccalli et al., The Vilsmeier-Haack Reaction of Isoxazolin-5-ones. Synthesis and Reactivity of 2-(Dialkylamino)-1,3-oxazin-6-ones, J. Org. Chm. 1987, 52, 3426-3434 (Dec. 31, 1987).
Dong Xue, et al., Transfer Hydrogenation of Activated CdC Bonds Catalyzed by Ruthenium Amido Complexes: Reaction Scope, Limitation, and Enantioselectivity, J. Org. Chem. 2005, 70, 3584-3591 (Apr. 2, 2005).
Bo Peng, et al., Nucleophilic Dearomatization of Chloromethyl Naphthalene Derivatives via η3-Benzylpalladium Intermediates: A New Strategy for Catalytic Dearomatization, Organic Letters, 2011, vol. 13, No. 19, 5402-5405 (Sep. 13, 2011).
Saurabh C. Patankar, et al., Cascade engineered synthesis of ethyl benzyl acetoacetate and methylisobutyl ketone (MIBK) on novel multifunctional catalyst, Journal of Molecular Catalysis A: Chemical 409 (2015) 171-182 (Aug. 21, 2015).

* cited by examiner

*Primary Examiner* — Jafar F Parsa
*Assistant Examiner* — Blaine G Doletski
(74) *Attorney, Agent, or Firm* — SZDC Law P.C.

(57) ABSTRACT

Disclosed are a reduction method and reduction product of an alkenyl active methylene compound. The reduction reaction comprises the following steps: taking an alkenyl active methylene compound as a substrate, a metal hydride as a reducing agent, and a palladium compound as a catalyst, performing a reduction reaction to obtain a reduction product, and then reducing the alkenyl active methylene compound. The reduction system is a simple method for reducing the alkenyl active methylene compound, and the used hydride and palladium compound catalyst are both reagents that could easily be obtained in a laboratory. Compared with conventional hydrogen hydrogenation methods and reduction methods of reducing agents, the method is easier to operate, higher in safety, mild in conditions, and high in reaction yield, a reaction in a one-pot two-step manner can be achieved, and high atom economy and step economy can be obtained.

5 Claims, No Drawings

REDUCTION METHOD AND REDUCTION PRODUCT OF ALKENYL ACTIVE METHYLENE COMPOUND

This application is a Continuation Application of PCT/CN2018/105597, filed on Sep. 13, 2018, which is incorporated by reference for all purposes as if fully set forth herein.

TECHNICAL FIELD

The invention relates to the technical field of organic synthesis, and particularly relates to the application of metal hydride/palladium compound catalyst system in the reduction of alkenyl active methylene compounds and one-pot reaction.

BACKGROUND TECHNIQUE

Sodium hydride is a strong base often used in laboratories and industries. For a long time, there have been few reports about its use as a reducing agent, and existing reactions require a large excess of reducing agent (3 equivalents), and at least 2 equivalents of sodium iodide are used as accelerators. Reduction of alkenyl active methylene compounds is a common chemical conversion to generate corresponding monoalkyl-substituted active methylene compounds; this type of reaction is generally carried out using hydrogen/palladium carbon conditions; in addition, some hydrogen teagents, such as [(Ph$_3$P)CuH]$_6$ (Stryker reagent), R$_3$SiH, Hantzsch ester, etc. can also complete the reduction of this electron-deficient double bond. However, these reducing conditions are either dangerous, such as explosive hydrogen, or the reagents are more expensive, the reaction lacks atomic economy, and more waste needs to be processed after the reaction, such as [(Ph$_3$P)CuH]$_6$ (Stryker reagent), R$_3$SiH, Hantzsch ester, etc., or need to treat a large amount of wastewater after some reactions, so there are certain limitations in industrial applications.

TECHNICAL PROBLEM

The technical problem to be solved by the present invention is to provide an application of a metal hydride/palladium compound catalytic reduction system, thereby providing a new method for reducing alkenyl active methylene compounds, and the application of this method in a one-pot reaction.

TECHNICAL SOLUTIONS

The technical means for realizing the above-mentioned reduction of an alkenyl-active methylene compound mentioned above uses metal hydride as a reducing agent, palladium and its salts as a catalyst, and reacts in a solvent to obtain a double-bonded reduction product. Specific technical solutions are as follows:

An application of metal hydride/palladium compound catalytic reduction system in reduction of alkenyl active methylene compound.

A method for reducing alkenyl active methylene compound uses an alkenyl active methylene compound as substrate, a metal hydride as a reducing agent, a palladium compound as a catalyst, and reduces to obtain a reduction product, and reduction of the alkenyl active methylene compound is completed;

In the technical solution above, after the reduction reaction, saturated ammonium chloride aqueous solution is added to stop the reaction, and then the product is subjected to extraction, drying, rotary evaporation, and column chromatography to obtain the reduction product.

In the present invention, the alkenyl active methylene compound has the following structure:

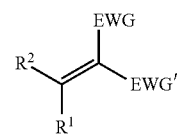

Wherein, R$^1$, R$^2$ are independently selected from the group consisting of hydrogen, alkyl, phenyl, substituted phenyl, naphthyl, pyridyl, and quinolinyl; EWG is selected from the group consisting of ester, keto, and amide; EWG' is selected from the group consisting of hydrogen, ester, keto, and amide.

In the structure of the alkenyl active methylene compound, the alkyl group may be a methyl group, and the substituted phenyl group may be a halogen-substituted phenyl group or a methoxy-substituted phenyl group.

In the present invention, the metal hydride comprises sodium hydride, lithium hydride, potassium hydride, calcium hydride, and the palladium compound includes palladium chloride, palladium acetate, Pd(MeCN)$_2$Cl$_2$, [(η$^3$-C$_3$H$_5$)PdCl]$_2$, Pd(TFA)$_2$, Pd(dppp)Cl$_2$, Pd$_2$(dba)$_3$, Pd(C$_6$H$_5$CN)$_2$Cl$_2$, Pd(OH)$_2$, Pd/C, Pd(PPh$_3$)$_4$, Pd(PPh$_3$)$_2$Cl$_2$, preferably, palladium chloride and palladium acetate, and more preferably, palladium chloride.

In the present invention, the molar ratio of the palladium compound:metal hydride:alkenyl active methylene compound is (0.01 to 1) (1 to 5) 1. Preferably, the molar ratio is (0.03 to 0.1):(1 to 3):1, and more preferably, the molar ratio is 0.05:(1.5 to 2.5):1, and even more preferably, the molar ratio is 0.05:2:1.

In the present invention, the reduction of the alkenyl active methylene compound is performed under the protection of nitrogen atmosphere; the solvent includes DMA (N,N-dimethylacetamide), DMF, THF, DME, or dioxane.

In the present invention, the temperature of the reduction of alkenyl active methylene compound is −50° C. to 120° C., preferably, 0 to 50° C.; the time of reduction is 0.3 to 10 hours, preferably, 0.5 to 5 hours, and more preferably, 45 min.

Beneficial Effects

The sodium hydride/palladium reduced alkenyl active methylene compound has the following advantages: 1) Compared with sodium borohydride, sodium hydride is cheaper (industrially, sodium borohydride is prepared from sodium hydride as a raw material); compared with hydrogen/palladium carbon reduction, the sodium hydride method is safer; 2) Sodium hydride has a small molecular weight and simple composition, and the amount used in the reaction is small, so using sodium hydride as a reducing agent is an atomic economic method; by-products includes harmless sodium salt, and no other waste is generated; 3) The product of the alkenyl active methylene compound reduced by sodium hydride is the sodium salt before the post-treatment, which is different from the existing reduction methods. Reactive sodium salts can continue to react with electrophilic reagents to obtain disubstituted products, which expands the application of alkenyl active methylene compounds. And in this one-pot reaction, the reducing and basic properties of sodium hydride are fully utilized, greatly improving the atomic economy and step economy of the reaction, and reducing the reaction cost.

The technical scheme of the present invention can be specifically described as follows: under the protection of nitrogen, stirring suspended palladium compound and metal hydride in a solvent, then adding the substrate alkenyl active methylene compound, the reaction being performed at −50° C. to 120° C. for 0.3 to 10 hours, the reaction being stopped by adding a saturated aqueous ammonium chloride solution, extracted with solvent, evaporated to dryness, and purified by column chromatography to obtain the product.

It is a simple way the reduction system for reducing the alkenyl active methylene compound in the invention, the hydride and palladium compound catalyst are easily got in the laboratory. Compared with conventional hydrogen hydrogenation methods and reducing agents with reduction, this method is more convenient, much higher in safety, in addition it is mild in condition but high in reaction yield. It has highly atomic economy and step economy with "a pot with two steps."

EMBODIMENTS OF THE INVENTION

Example 1

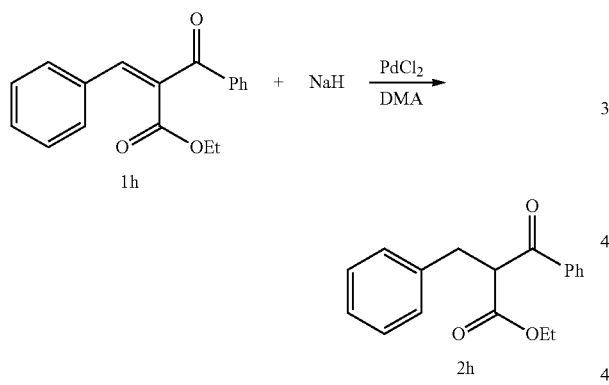

Under the protection of nitrogen, palladium chloride (1.7 mg, 0.01 mmol, 5 mol %) and sodium hydride (60% in oil, 16 mg, 0.4 mmol, 2 equiv.) were stirred and suspended in DMA (1.0 mL) for 5 min at room temperature, and then the compound 1h (0.2 mmol) in DMA (0.5 mL) was added. The reaction was performed at room temperature for 45 min. The reaction was quenched by adding a saturated aqueous ammonium chloride solution. The product was subjected to extraction with ethyl acetate, combining the extract, drying with sodium sulphate, rotary evaporation, and column chromatography to obtain the product 2h with a yield of 99%.
$^1$H NMR (400 MHz, CDCl$_3$): δ 8.00 (d, J=7.7 Hz, 2H), 7.60 (t, J=7.3 Hz, 1H), 7.48 (t, J=7.6 Hz, 2H), 7.34-7.26 (m, 4H), 7.25-7.19 (m, 1H), 4.66 (t, J=7.3 Hz, 1H), 4.18-4.08 (m, 2H), 3.43-3.30 (m, 2H), 1.15 (t, J=7.1 Hz, 3H). $^{13}$C NMR (151 MHz, CDCl$_3$): δ 194.61, 169.40, 138.57, 136.33, 133.64, 129.06, 128.81, 128.78, 128.65, 126.76, 61.63, 56.32, 34.89, 14.07. LR-MS (ESI): m/z 283.2 [M+H]+.

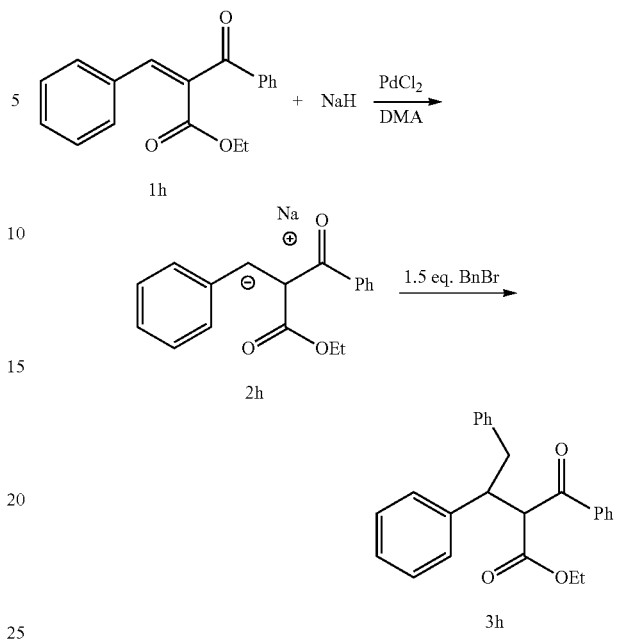

Under the protection of nitrogen, palladium chloride (1.7 mg, 0.01 mmol, 5 mol %) and sodium hydride (60% in oil, 16 mg, 0.4 mmol, 2 equiv.) were stirred and suspended in DMA (1.0 mL) for 5 min at room temperature, then the compound 1h (0.2 mmol) in DMA (0.5 mL) was added. The reaction was performed at room temperature for 45 min, and benzyl bromide (1.5 eq.) was added. After the reaction was complete, the reaction was quenched by adding a saturated aqueous ammonium chloride solution. The reaction mixture was extract with ethyl acetate. The organic phase was collected and dried by rotary evaporation. Column chromatography gave the compound 3 h with a yield of 98%.

Example 2

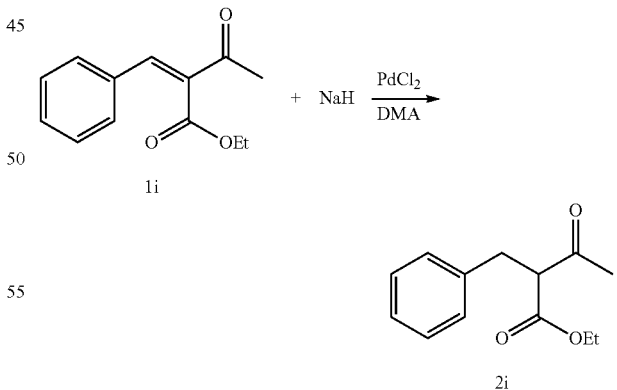

Under the protection of nitrogen, palladium chloride (34 mg, 0.01 mmol, 5 mol %) and sodium hydride (60% in oil, 16 mg, 0.4 mmol, 2 equiv.) were stirred and suspended in DMA (1.0 mL) for 0.75 h at room temperature, and then the compound 1i (0.2 mmol) in DMA (0.5 mL) was added. The reaction was quenched by adding a saturated aqueous ammonium chloride solution. The reaction mixture was extract with ethyl acetate. The organic phase was collected and dried by rotary evaporation. Column chromatography gave the compound 2i with a yield of 98%. $^1$H NMR (400 MHz, CDCl$_3$): δ 7.31-7.14 (m, 5H), 4.14 (q, J=7.0 Hz, 2H), 3.78 (t, J=7.6 Hz, 1H), 3.16 (d, J=7.5 Hz, 2H), 2.19 (s, 3H), 1.20 (t, J=7.1 Hz, 3H). $^{13}$C NMR (151 MHz, CDCl$_3$): δ 202.63, 169.22, 138.23, 128.89, 128.67, 126.78, 61.60, 61.42, 34.08, 29.77, 14.14. LR-MS (ESI): m/z 221.1 [M+H]+.

Example 3

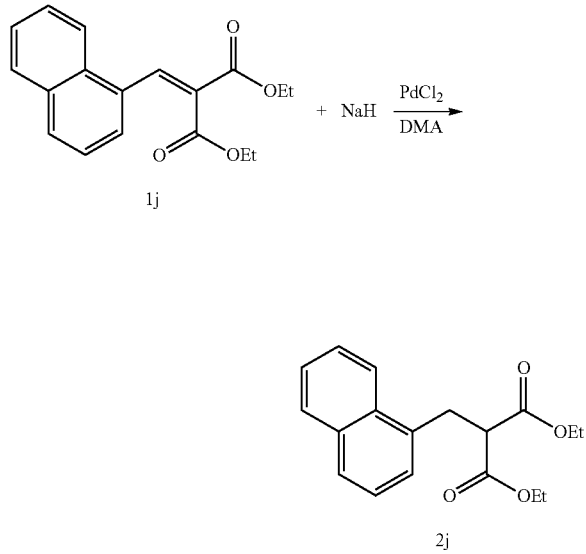

Under the protection of nitrogen, stirring suspended palladium chloride (1.7 mg, 0.01 mmol, 5 mol %) and sodium hydride(60% in oil, 16 mg, 0.4 mmol, 2 equiv), are in DMA (1.0 mL) for 5 min at room temperature, then add the compound 1j (0.2 mmol) in the solution of DMA (0.5 mL), the reaction is performed at room temperature for 45 min, the reaction is stopped by adding the solution of saturated aqueous ammonium chloride, the product is subjected extraction with ethyl acetate, combine extract, drying with sodium sulphate, rotary evaporation, and column chromatography to obtain the product 2j with a yield of 97%.

Under the protection of nitrogen, palladium chloride (1.7 mg, 0.01 mmol, 5 mol %) and sodium hydride (60% in oil, 16 mg, 0.4 mmol, 2 equiv.) were stirred and suspended in DMA (1.0 mL) for 5 min at room temperature, and then the compound 1j (0.2 mmol) in DMA (0.5 mL) was added. The reaction was quenched by adding a saturated aqueous ammonium chloride solution. The reaction mixture was extract with ethyl acetate. The organic phase was collected and dried by rotary evaporation. Column chromatography gave the compound 2j with a yield of 97%. $^1$H NMR (400 MHz, CDCl$_3$): δ 8.04 (d, J=8.2 Hz, 1H), 7.86 (d, J=7.8 Hz, 1H), 7.78-7.70 (m, 1H), 7.58-7.46 (m, 2H), 7.37 (d, J=4.4 Hz, 2H), 4.24-4.07 (m, 4H), 3.84 (t, J=7.4 Hz, 1H), 3.71 (d, J=7.4 Hz, 2H), 1.19 (t, J=7.0 Hz, 6H). $^{13}$C NMR (101 MHz, CDCl$_3$): δ 169.17, 134.03, 133.95, 131.71, 129.10, 127.79, 127.30, 126.40, 125.77, 125.53, 123.35, 61.65, 53.01, 31.94, 14.14. LR-MS (ESI): m/z 301.1 [M+H]+.

Example 4

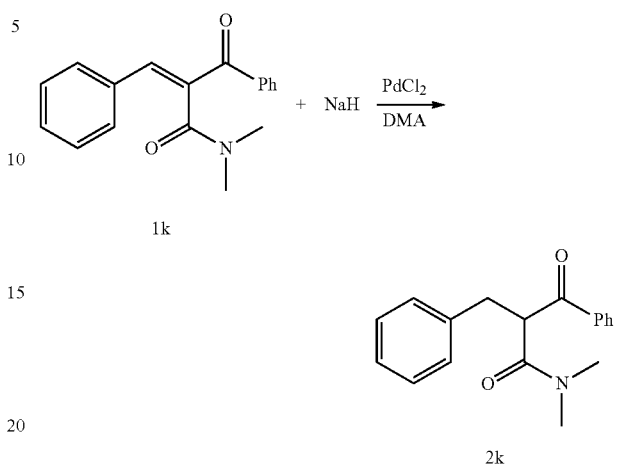

Under the protection of nitrogen, stirring suspended palladium chloride (17 mg, 0.01 mmol, 5 mol %) and sodium hydride (60% in oil, 16 mg, 0.4 mmol, 2 equiv), are in DMA (1.0 mL) for 5 min at room temperature, then add the compound 1k (0.2 mmol) in the solution of DMA (0.5 mL), the reaction is performed at room temperature for 0.75 h, the reaction is stopped by adding the solution of saturated aqueous ammonium chloride, the product is subjected extraction with ethyl acetate, combine extract, drying with sodium sulphate, rotary evaporation, and column chromatography to obtain the product 2k with a yield of 97%.

Under the protection of nitrogen, palladium chloride (1.7 mg, 0.01 mmol, 5 mol %) and sodium hydride (60% in oil, 16 mg, 0.4 mmol, 2 equiv.) were stirred and suspended in DMA (1.0 mL) for 5 min at room temperature, and then the compound 1k (0.2 mmol) in DMA (0.5 mL) was added. The reaction was quenched by adding a saturated aqueous ammonium chloride solution. The reaction mixture was extract with ethyl acetate. The organic phase was collected and dried by rotary evaporation. Column chromatography gave the compound 2k with a yield of 97%. $^1$H NMR (400 MHz, CDCl$_3$): δ 7.89 (d, J=7.1 Hz, 2H), 7.55 (t, J=6.6 Hz, 2H), 7.44 (d, J=7.2 Hz, 2H), 7.31-7.17 (m, 5H), 4.70-4.55 (m, 1H), 3.43-3.26 (m, 2H), 2.90 (s, 3H), 2.77 (s, 3H). $^{13}$C NMR (101 MHz, CDCl$_3$): δ 195.34, 169.30, 139.32, 136.22, 133.41, 129.20, 128.90, 128.64, 128.35, 126.75, 54.73, 37.40, 36.01, 35.54. LR-MS (ESI): m/z 282.2 [M+H]+.

The invention claimed is:
1. A method of reducing an alkenyl active methylene compound comprising:
reacting the alkenyl active methylene compound with a metal hydride in the presence of a palladium compound in an organic solvent,
wherein the alkenyl active methylene compound has the following structure:

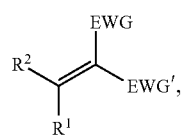

$R^1$ and $R^2$ are independently selected from the group consisting of hydrogen, alkyl, phenyl, substituted phenyl, naphthyl, pyridyl, and quinolinyl, EWG is selected from the group consisting of —$COC_6H_5$, —$COOCH_2CH_3$, —$COCH_3$, and —$CON(CH_3)_2$, and EWG' is selected from the group consisting of hydrogen, —$COC_6H_5$, —$COOCH_2CH_3$, —$COCH_3$, and —$CON(CH_3)_2$;

wherein the metal hydride is sodium hydride, lithium hydride, potassium hydride, or calcium hydride;

wherein the palladium compound is palladium chloride, palladium acetate, $Pd(MeCN)_2Cl_2$, $[(\eta^3\text{-}C_3H_5)PdCl]_2$, $Pd(TFA)_2$, $Pd(dppp)Cl_2$, $Pd_2(dba)_3$, $Pd(C_6H_5CN)_2Cl_2$, $Pd(OH)_2$, Pd/C, $Pd(PPh_3)_4$, or $Pd(PPh_3)_2Cl_2$; and wherein the organic solvent is DMA (dimethylacetamide), DMF (dimethylformamide), THF (tetrahydrofuran), DME (dimethoxyethane), or dioxane.

2. The method according to claim 1, wherein a molar ratio of the palladium compound:the metal hydride:the alkenyl active methylene compound is 0.05:(1.5 to 2.5):1.

3. The method according to claim 2, wherein a molar ratio of the palladium compound:the metal hydride:the alkenyl active methylene compound is 0.05:2:1.

4. The method according to claim 1, wherein the reduction of the alkenyl active methylene compound is performed under the protection of nitrogen atmosphere, at 0° C. to 50° C., for 0.5 to 5 hours.

5. The method according to claim 4, wherein the reduction of the alkenyl active methylene compound is at room temperature, for 45 minutes.

\* \* \* \* \*